United States Patent
Dejima

(10) Patent No.: US 9,949,616 B2
(45) Date of Patent: Apr. 24, 2018

(54) ENDOSCOPIC SURGERY DEVICE, METHOD OF INSERTING ENDOSCOPE AND TREATMENT TOOL, AND METHOD OF REMOVING ENDOSCOPE AND TREATMENT TOOL

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 130 days.

(21) Appl. No.: 14/864,892

(22) Filed: Sep. 25, 2015

(65) Prior Publication Data

US 2016/0022118 A1 Jan. 28, 2016

Related U.S. Application Data

(63) Continuation of application No. PCT/JP2014/058774, filed on Mar. 27, 2014.

(30) Foreign Application Priority Data

Mar. 29, 2013 (JP) ................................. 2013-074010

(51) Int. Cl.
*A61B 1/00* (2006.01)
*A61B 17/34* (2006.01)

(52) U.S. Cl.
CPC ...... *A61B 1/00087* (2013.01); *A61B 1/00154* (2013.01); *A61B 17/3421* (2013.01);
(Continued)

(58) Field of Classification Search
CPC ............ A61B 1/00087; A61B 17/3421; A61B 17/3462; A61B 1/00154;
(Continued)

(56) References Cited

U.S. PATENT DOCUMENTS 5,569,205 A * 10/1996 Hart .................... A61B 17/3462
604/167.03
2005/0119525 A1* 6/2005 Takemoto .......... A61B 1/00154
600/114

(Continued)

FOREIGN PATENT DOCUMENTS

JP 2004-141486 5/2004
JP 2004-180858 7/2004

(Continued)

OTHER PUBLICATIONS

"Office Action of Japan Counterpart Application" with English translation thereof, dated Aug. 29, 2016, pp. 1-8.

(Continued)

*Primary Examiner* — Genja Frankhert
(74) *Attorney, Agent, or Firm* — JCIPRNET

(57) ABSTRACT

An endoscope and a treatment tool which are inserted into an outer tube can move back and forth in interlock with each other, and an operation part of the treatment tool can be prevented from interfering with a proximal end of the endoscope when inserting the treatment tool into the outer tube. An endoscopic surgery device satisfies the following expressions: $Lt \leq Ls < Lh$, and $Lh \geq Ls1 + Ls + t$, where Lt is a length of the outer tube, Ls is a length of a hard part of the insertion part of the endoscope, Lh is a length of a hard part of the insertion part of the treatment tool, Ls1 is a minimum projection length of a distal end of the insertion part of the treatment tool with respect to a distal end of the insertion part of the endoscope, and t is an allowance amount.

10 Claims, 13 Drawing Sheets

(52) U.S. Cl.
CPC .. *A61B 17/3462* (2013.01); *A61B 2017/3441* (2013.01); *A61B 2017/3445* (2013.01); *A61B 2017/3466* (2013.01)

(58) Field of Classification Search
CPC .... A61B 2017/3466; A61B 2017/3441; A61B 2017/3445; A61B 1/00135; A61B 600/106; A61B 600/114; A61B 1/018; A61B 1/0014; A61B 1/100147; A61B 17/29
See application file for complete search history.

(56) References Cited

U.S. PATENT DOCUMENTS

| | | | | |
|---|---|---|---|---|
| 2007/0239171 | A1* | 10/2007 | Stefanchik | A61B 17/0218 606/113 |
| 2008/0051631 | A1* | 2/2008 | Dejima | A61B 1/0052 600/114 |
| 2008/0281299 | A1* | 11/2008 | Menn | A61B 1/0014 606/1 |
| 2011/0124960 | A1 | 5/2011 | St. Onge et al. | |
| 2011/0230713 | A1 | 9/2011 | Kleemann et al. | |
| 2015/0080650 | A1 | 3/2015 | Dejima et al. | |

FOREIGN PATENT DOCUMENTS

| | | |
|---|---|---|
| JP | 2012-501695 | 1/2012 |
| WO | 2013/176167 | 11/2013 |

OTHER PUBLICATIONS

"Written Opinion of the International Searching Authority" of PCT/JP2014/058774, dated May 13, 2014, with English translation thereof, pp. 1-13, in which two of the listed references (JP2012-501695 and WO 2013/176167) were cited.

* cited by examiner

ENDOSCOPIC SURGERY DEVICE, METHOD OF INSERTING ENDOSCOPE AND TREATMENT TOOL, AND METHOD OF REMOVING ENDOSCOPE AND TREATMENT TOOL

CROSS-REFERENCE TO RELATED APPLICATIONS

This application is a Continuation of PCT International Application No. PCT/JP2014/058774 filed on Mar. 27, 2014, which claims priority under 35 U.S.C. § 119(a) to Japanese Patent Application No. 2013-074010 filed on Mar. 29, 2013. Each of the above application(s) is hereby expressly incorporated by reference, in its entirety, into the present application.

BACKGROUND OF THE INVENTION

Field of the Invention

The present invention relates to an endoscopic surgery device, a method of inserting an endoscope and a treatment tool into an outer tube, and a method of removing an endoscope and a treatment tool therefrom, and more particularly to an endoscopic surgery device including an endoscope, a treatment tool, and an outer tube, a method of inserting the endoscope and the treatment tool into the outer tube, and a method of removing the endoscope and the treatment tool therefrom.

Description of the Related Art

In recent years, endoscopic surgery (such as laparoscopic cholecystectomy), in which an endoscope such as a laparoscope, and a treatment tool are inserted into an abdominal cavity through an outer tube inserted through an abdominal wall to treat a lesion site, has become widespread. Since an operative wound in this endoscopic surgery is smaller than an abdominal surgery, it is possible to shorten a postoperative bed rest period.

Japanese National Publication of International Patent Application No. 2012-501695 (hereinafter, referred to as PTL 1) discloses an endoscopic surgery device that includes an endoscope (laparoscope), a treatment tool (laparoscope forceps), and an outer tube (port) through which an insertion part (shank) of the endoscope and an insertion part (shank) of the treatment tool are moved back and forth.

The insertion part of each of the endoscope and the treatment tool is formed in an elongated linear shape. The insertion part of the endoscope is provided at its distal end with observation means (observation mechanism) including an objective lens, and the insertion part of the treatment tool is provided at its distal end with a treatment part (forceps). In addition, the insertion part of the endoscope is provided at its proximal end with a body coupled through a joint, and the insertion part of the treatment tool is provided at its proximal end with an operation part (operation mechanism) that operates the treatment part.

In addition, in the endoscopic surgery device of PTL 1, the distal end of the insertion part of the treatment tool projects to the outer side (inner side the body cavity) from the distal end of the insertion part of the endoscope than a distal end of the outer tube. Accordingly, it is possible to observe the treatment part of the treatment tool with the observation means of the endoscope.

Further, in the endoscopic surgery device of PTL 1, the operation part of the treatment tool projects to the inner side (outer side the body cavity) from the body of the endoscope than a proximal end of the outer tube. Accordingly, a surgeon can perform operation without interference between the body of the endoscope and the operation part of the treatment tool.

That is, PTL 1 discloses the endoscopic surgery device in which the insertion part of the treatment tool is made longer than the insertion part of the endoscope.

Furthermore, PTL 1 also describes the body of the endoscope that is arranged outside an operation area of the operation part of the treatment part by means of a joint.

SUMMARY OF THE INVENTION

However, in the endoscopic surgery device of PTL 1, if the treatment part of the treatment tool is positioned outside a range of a field of view of the observation means of the endoscope, a complicated operation is required such that the insertion part of the endoscope is independently operated in a back-and-forth direction separately from the treatment tool to position the treatment part of the treatment tool inside the range of the field of view.

In addition, in the endoscopic surgery device of PTL 1, although it is possible to arrange the body of the endoscope outside the operation area of the operation part of the treatment part, the operation part of the treatment tool may interfere (contact) with the proximal end of the endoscope depending on an insertion direction of the treatment tool.

The present invention is made in light of the above-mentioned circumstances, and aims to provide: an endoscopic surgery device in which an insertion part of an endoscope inserted into an outer tube and an insertion part of a treatment tool can move back and forth in interlock with each other while reliably preventing interference between an operation part of the treatment tool and a proximal end of the endoscope at the time of insertion operation of the treatment tool into the outer tube; and a method of inserting an endoscope and a treatment tool into an outer tube, and a method of removing the endoscope and the treatment tool in which the endoscope and the treatment tool can be smoothly movable back and forth in the outer tube.

In order to achieve the object described above, one aspect of the present invention provides an endoscopic surgery device that includes: an endoscope which includes a linear insertion part and is configured to observe a body cavity; a treatment tool including a linear insertion part whose proximal end is provided with an operation part; and an outer tube which is configured to allow each of the insertion part of the endoscope and the insertion part of the treatment tool to be movable back and forth, and in which the insertion part of the treatment tool relatively is movable back and forth with an allowance with respect to the insertion part of the endoscope, wherein the endoscopic surgery device satisfies expressions of Lt≤Ls<Lh, and Lh≥Ls1+Ls+t, where Lt (mm) is a length of the outer tube, Ls (mm) is a length of a hard part of the insertion part of the endoscope, Lh (mm) is a length of a hard part of the insertion part of the treatment tool, Ls1 (mm) is a minimum projection length of a distal end of the insertion part of the treatment tool with respect to a distal end of the insertion part of the endoscope, and t (mm) is an allowance amount of the insertion part of the treatment tool with respect to the insertion part of the endoscope.

Features of the endoscopic surgery device of the one aspect of the present invention will be described below.

a) First Feature

The endoscopic surgery device includes an endoscope, a treatment tool, and an outer tube, and allows the endoscope to move in a back-and-forth direction in interlock with operation of the treatment tool in the back-and-forth direction if the treatment tool is operated so as to exceed an allowance amount at the time of operation of the treatment tool in the back-and-forth direction. As a result, it is possible to move an insertion part of the endoscope inserted into the outer tube and an insertion part of the treatment tool back and forth in interlock with each other. In addition, the insertion part of the treatment tool moves in an axial direction of the outer tube with a predetermined allowance amount with respect to the insertion part of the endoscope. Accordingly, if the insertion part of the treatment tool is moved in the back-and-forth direction within a range of the allowance amount, the endoscope does not move in the back-and-forth direction. By providing this allowance amount, slight movement of the treatment tool is not transmitted to the endoscope, whereby it is possible to provide a favorable endoscopic image without shake.

b) Second Feature

In order to observe a treatment part of the treatment tool by means of observation means of the endoscope, a projection length of a distal end of the insertion part of the treatment tool from a distal end of the outer tube is set equal to or longer than a projection length of a distal end of the insertion part of the endoscope from the distal end of the outer tube.

This endoscopic surgery device satisfies $Lt \leq Ls < Lh$, and $Lh \geq Ls1+Ls+t$, where $Lt$ is a length of the outer tube, $Ls$ is a length of a hard part of the insertion part of the endoscope, $Lh$ is a length of a hard part of the insertion part of the treatment tool, $Ls1$ is a minimum projection length of the distal end of the insertion part of the treatment tool with respect to the distal end of the insertion part of the endoscope, and $t$ is the allowance amount. That is, since the length $Lh$ of the hard part of the insertion part of the treatment tool is equal to or longer than a length obtained by totaling the projection length $Ls1$, the length $Ls$ of the insertion part of the endoscope and the allowance amount $t$, it is possible to reliably prevent an operation part of the treatment tool from interfering with a proximal end of the endoscope at the time of operation of inserting the treatment tool into the outer tube. In addition, if the treatment tool is moved in a back-and-forth direction beyond a range of the allowance amount $t$, because the endoscope also moves in the same direction in interlock with the treatment tool, the operation part of the treatment tool does not interfere with the proximal end of the endoscope.

In another aspect of the present invention, it is preferable that the minimum projection length $Ls1$ satisfy $Ls1 \geq 0$.

According to this aspect of the present invention, it is possible to observe a treatment part of the treatment tool by means of the observation device of the endoscope if $Ls1 \geq 0$ is satisfied.

In yet another aspect of the present invention, it is preferable that the minimum projection length $Ls1$ be a length with which at least the distal end of the insertion part of the treatment tool is positioned in an observation field of view of the endoscope.

According to this aspect of the present invention, it is possible to obtain an endoscopic image of the treatment part including the distal end of the insertion part of the treatment tool.

In yet another aspect of the present invention, it is preferable that a distance between centers of the insertion part of the endoscope and the insertion part of the treatment tool in the outer tube is set shorter than a distance between an axial center of the insertion part of the treatment tool and at least a part of the operation part of the treatment tool.

According to this aspect of the present invention, in order to reduce a diameter of the outer tube, the distance between centers of the insertion part of the endoscope and the insertion part of the treatment tool in the outer tube is set shorter than the distance between the axial center of the insertion part of the treatment tool and at least a part of the operation part of the treatment tool.

In yet another aspect of the present invention, it is preferable that the distal end of the insertion part of the treatment tool have a treatment part, and the operation part of the treatment tool is a handle part configured to operate the treatment part.

According to this aspect of the present invention, it is possible to remotely control the treatment part by operating the handle part of the treatment tool. As a result, even if the treatment tool is moved in the back-and-forth direction with respect to the outer tube, the handle part does not interfere with the proximal end of the insertion part of the endoscope.

In yet another aspect of the present invention, it is preferable that a flexible cable be coupled to the proximal end of the insertion part of the endoscope.

According to this aspect of the present invention, even if the treatment tool is moved in the back-and-forth direction with respect to the outer tube, the operation part does not interfere with the flexible cable of the endoscope.

In yet another aspect of the present invention, it is preferable that the distal end of the insertion part of the endoscope have an observation device. According to this aspect of the present invention, it is possible to acquire an endoscopic image of a body cavity by means of the observation device of the endoscope.

In yet another aspect of the present invention, it is preferable that a coupling member, which is configured to couple the insertion part of the endoscope to the insertion part of the treatment tool, include: a first movable object which is configured to be movable in the axial direction of the outer tube and hold the insertion part of the endoscope inserted into the outer tube; and a second movable object which is provided in the first movable object, configured to hold the insertion part of the treatment tool inserted into the outer tube, and move in the axial direction of the outer tube by the allowance amount with respect to the first movable object.

According to this aspect of the present invention, the coupling member may include the first movable object and the second movable object.

In yet another aspect of the present invention, it is preferable that the first movable object be engaged with the outer tube with a first frictional force (F1), and that the second movable object be engaged with the insertion part of the treatment tool with a second frictional force (F2) greater than the first frictional force (F1), engaged with the first movable object with a third frictional force (F3) less than the first frictional force (F1) and slide against the first movable object by the allowance amount.

According to this aspect of the present invention, if a relationship of the frictional force is set to F2>F1>F3, the endoscope smoothly moves in the back-and-forth direction in interlock with movement of the treatment tool in the back-and-forth direction, and the treatment tool smoothly slides against the endoscope in the axial direction of the outer tube by the allowance amount.

In order to achieve the object described above, the present invention provides a method of inserting an endoscope and a treatment tool into an outer tube by using the endoscopic surgery device of the present invention, the method including: a first insertion step of inserting an insertion part of the endoscope into an outer tube; and a second insertion step of inserting an insertion part of the treatment tool into the outer tube into which the insertion part of the endoscope has been inserted.

According to this aspect of the present invention, first the insertion part of the endoscope, whose insertion part has a short length, is inserted into the outer tube. As a result, it is possible to smoothly insert the endoscope without interference with the treatment tool when the insertion part of the endoscope is inserted. After that, the insertion part of the treatment tool, whose insertion part has a long length, is inserted. When the insertion part of the treatment tool is inserted, the insertion part of the endoscope does not obstruct the insertion part of the treatment tool. Thus, it is possible to smoothly insert the insertion part of the treatment tool into the outer tube without bending the insertion part of the endoscope.

In order to achieve the object described above, the present invention provides a method of removing an endoscope and a treatment tool from an outer tube by using the endoscopic surgery device of the present invention, the method including: a first removal step of removing an insertion part of the treatment tool from the outer tube; and a second removal step of removing an insertion part of the endoscope from the outer tube from which the insertion part of the treatment tool has been removed.

According to this aspect of the present invention, after the insertion part of the treatment tool, whose insertion part had a long length, is first removed from the outer tube, and then the insertion part of the endoscope, whose insertion part has a short length, is removed. Thus, the endoscope does not interfere with the treatment tool at the time of removal. In addition, when the insertion part of the treatment tool is removed, because the insertion part of the endoscope does not obstruct the insertion part of the treatment tool, it is possible to smoothly remove the treatment tool from the outer tube without bending the insertion part of the endoscope.

According to the endoscopic surgery device of the present invention, it is possible to move the insertion part of the endoscope and the insertion part of the treatment tool, which are inserted into the outer tube, back and forth in interlock with each other. In addition, it is possible to reliably prevent interference between an operation part of the treatment tool and a proximal end of the endoscope at the time of insertion operation of the treatment tool into the outer tube.

Moreover, according to the method of inserting the treatment tool and the endoscope into the outer tube, and the method of removing the treatment tool and the endoscope from the outer tube, of the present invention, it is possible to move endoscope and the treatment tool to smoothly move back and forth with respect to the outer tube.

DETAILED DESCRIPTION OF THE EMBODIMENTS

Hereinafter, with reference to the accompanying drawings, a preferable embodiment of each of an endoscopic surgery device, a method of inserting an endoscope and a treatment tool into an outer tube, and a method of removing the endoscope and the treatment tool from the outer tube, of the present invention, will be described in detail.

Figure 1:
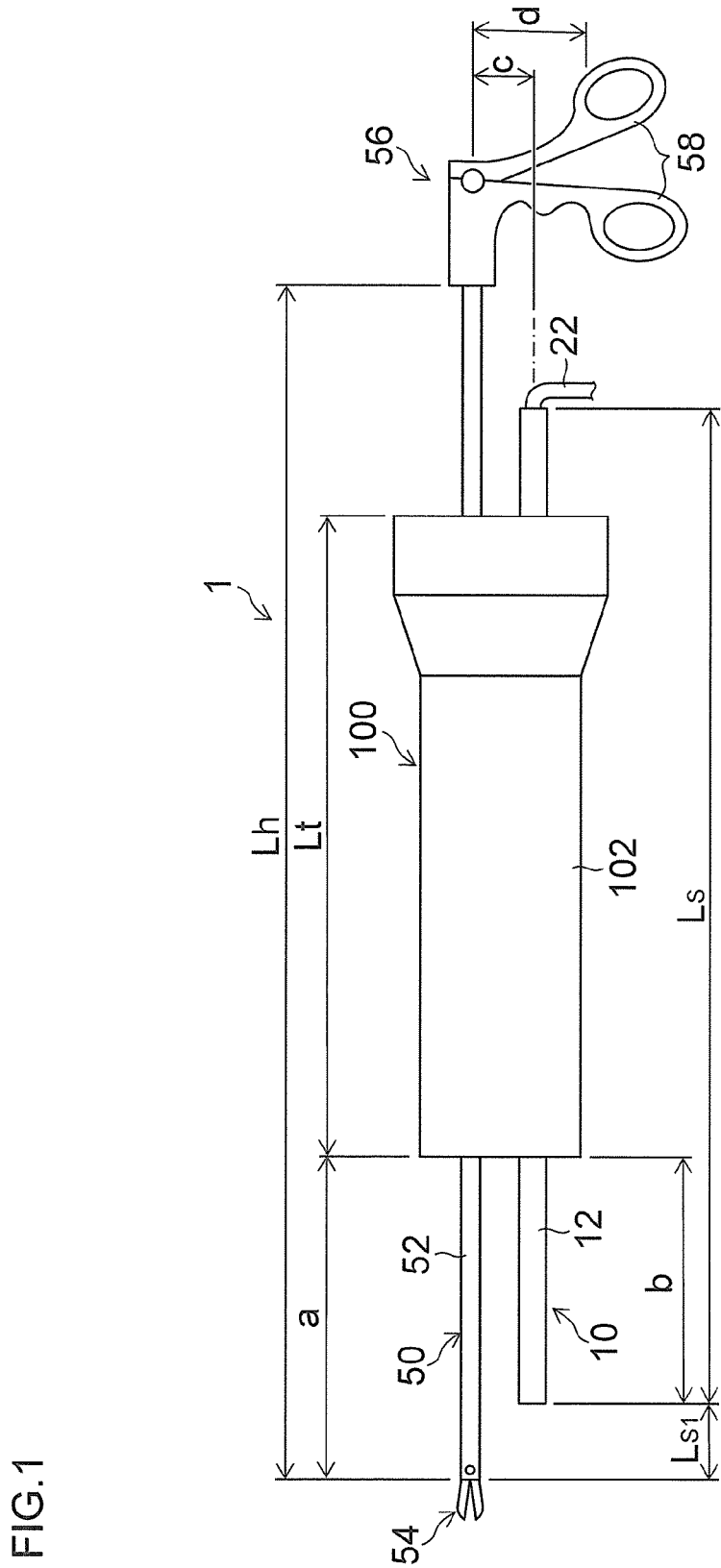
FIG. 1 is a schematic configuration diagram of an endoscopic surgery device of an embodiment.

FIG. 1 is a schematic configuration diagram of an endoscopic surgery device 1 in accordance with an embodiment.

<<Configuration of Endoscopic Surgery Device 1>>

The endoscopic surgery device 1 includes: an endoscope 10 that is to be inserted into a body cavity of a patient to observe inside the body cavity; a treatment tool 50 that is to be inserted into the body cavity of the patient to perform required treatment; and an outer tube 100 that guides the endoscope 10 and the treatment tool 50 into the body cavity of the patient. In FIG. 1, Ls, Lh, and Lt designate a length of a hard part of a linear insertion part 12 of the endoscope 10, a length of a hard part of a linear insertion part 52 of the treatment tool 50, and a length of the outer tube 100, respectively. The endoscopic surgery device 1 of FIG. 1 has a relationship among Ls, Lh, and Lt as follows: Lt<Ls<Lh, but may have a relationship as follows: Lt≤Ls<Lh.

[Endoscope 10]

Figure 2:
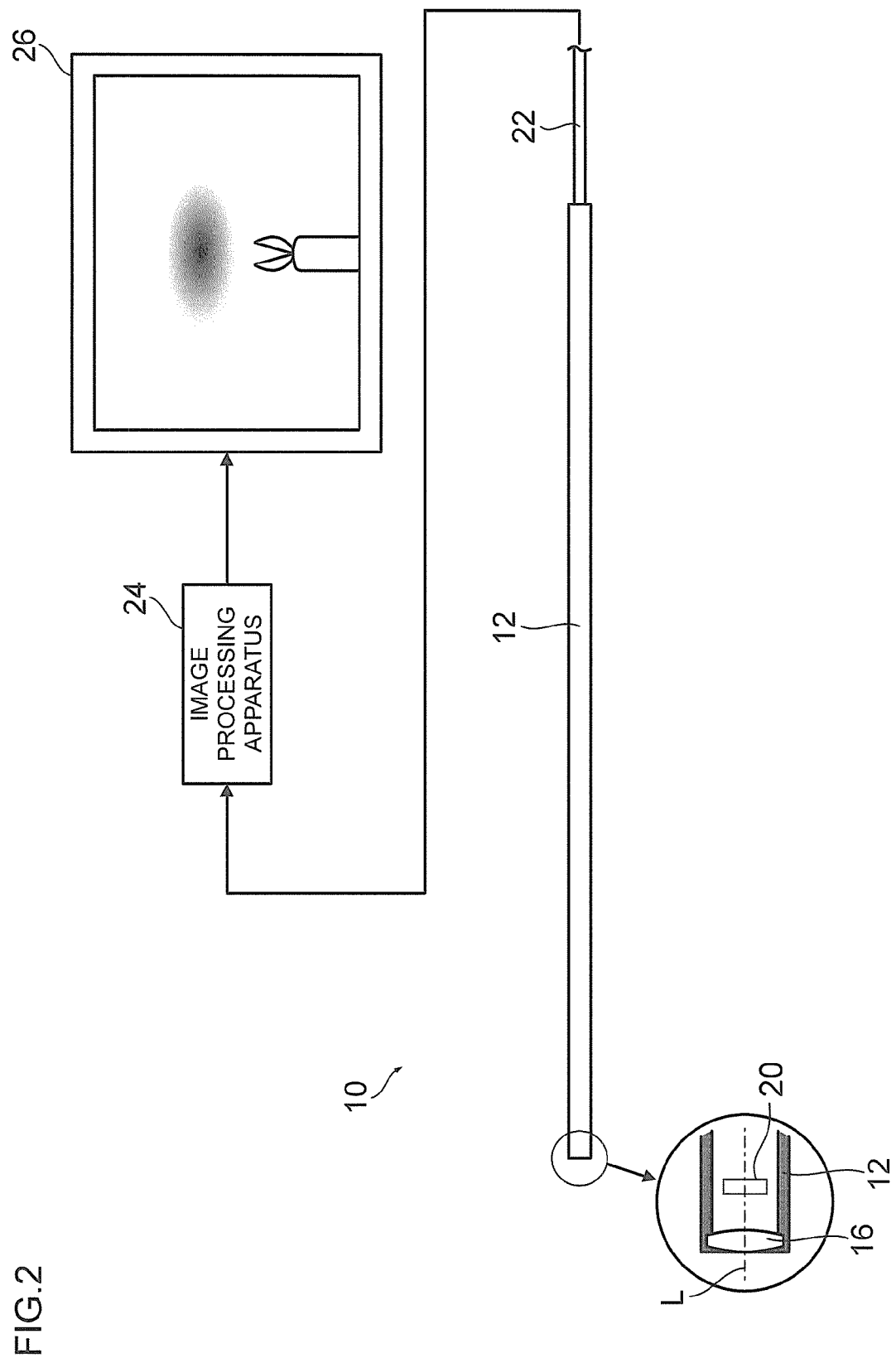
FIG. 2 is a schematic configuration diagram showing an example of an endoscope.

FIG. 2 is a schematic configuration diagram showing an example of the endoscope 10.

The endoscope 10 is a direct-view-type rigid endoscope such as a laparoscope. The endoscope 10 includes the linear insertion part 12 that is to be inserted into a body cavity of a patient, and a flexible cable 22 that is connected to a proximal end of the insertion part 12.

The insertion part 12 is integrally provided at its distal end with an objective lens 16 and an imaging element 20 serving as imaging means (such as a charge coupled device (CCD), and a complementary metal-oxide semiconductor (CMOS)). In an imaging surface of the imaging element 20, an observation image through the objective lens 16 is imaged, and an image signal generated by the imaging element 20 is outputted to an image processing apparatus 24 through the cable 22. The image processing apparatus 24 captures the image signal outputted from the imaging element 20 and applies various kinds of processing to the captured signal to generate a video signal that can be outputted to a display 26. The objective lens 16 and the imaging element 20 constitute observation means. Instead of the observation means, optical fibers serving as optical transmission means may be used.

The image processing apparatus 24 is connected to the display 26, such as a liquid crystal monitor. The image processing apparatus 24 generates a video signal so that the video signal is outputted to the display 26 to be displayed in a screen of the display 26 as an endoscope photographing image.

The endoscope 10 of the present example is provided with no illumination means. Illumination is performed by using separated means such as a needle light. Elimination of built-in illumination means from the endoscope enables to reduce an outer diameter of the insertion part 12 of the endoscope 10. Accordingly, it is possible to reduce an outer diameter of the outer tube 100 to reduce invasion applied to a body wall of a patient.

[Needle Light 30]

Figure 3:
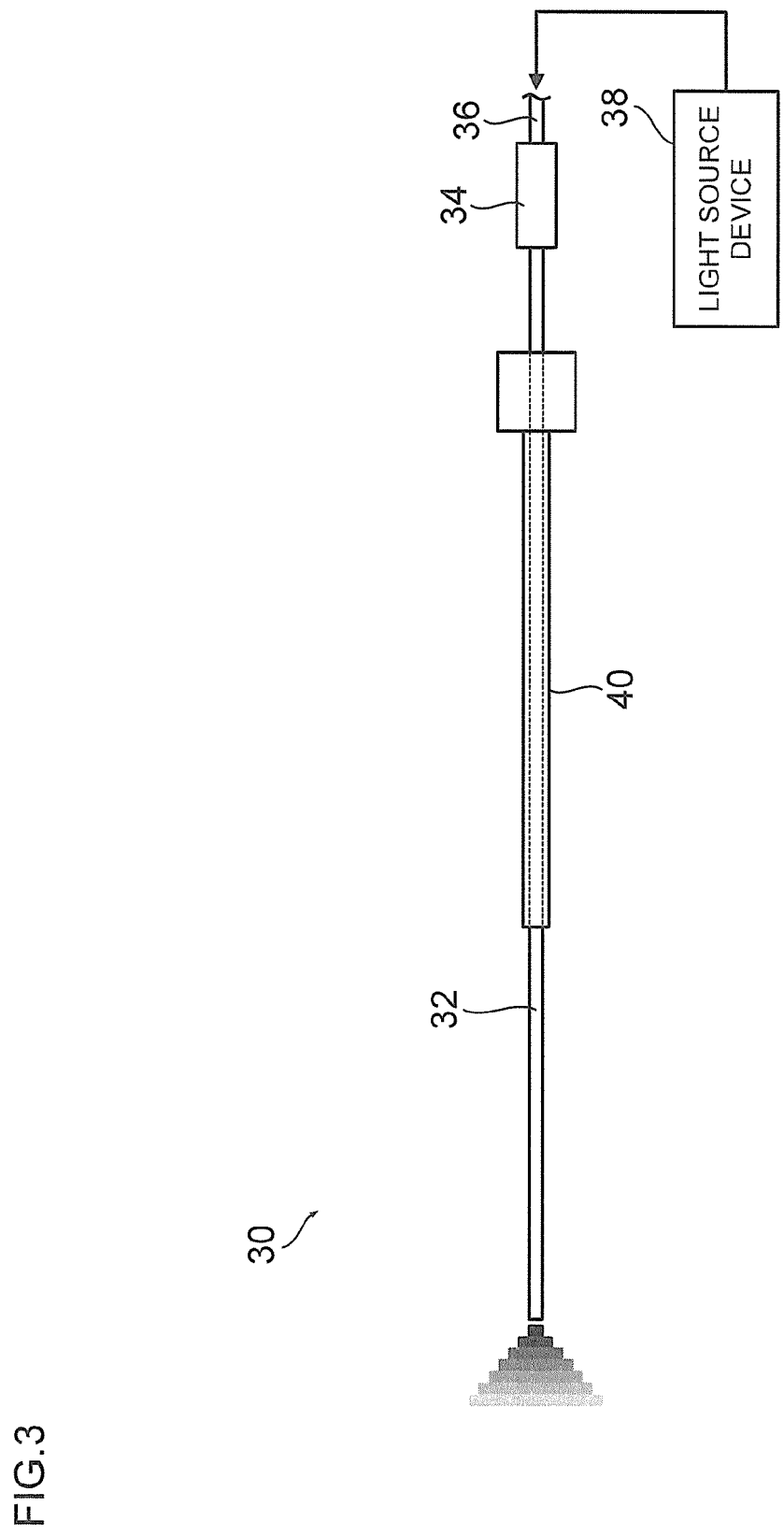
FIG. 3 is a schematic configuration diagram showing an example of a needle light.

FIG. 3 is a schematic configuration diagram showing an example of a needle light 30.

The needle light 30 is inserted into a body cavity of a patient to irradiate the inside of the body cavity with illumination light.

The needle light 30 is provided with a linear insertion part 32. The insertion part 32 is provided at its distal end with an illumination window (not shown) through which illumination light is emitted in an axial direction. The insertion part 32 houses inside an optical fiber bundle which transmits the illumination light emitted through the illumination window.

The needle light 30 is provided at its proximal end with a connection part 34 that is connected to a light source device 38 through a flexible cable 36. The illumination light to be emitted through the illumination window is supplied from the light source device 38.

The needle light 30 is inserted into a body cavity through a trocar 40 for a needle light, for example.

[Treatment Tool 50]

Figure 4:
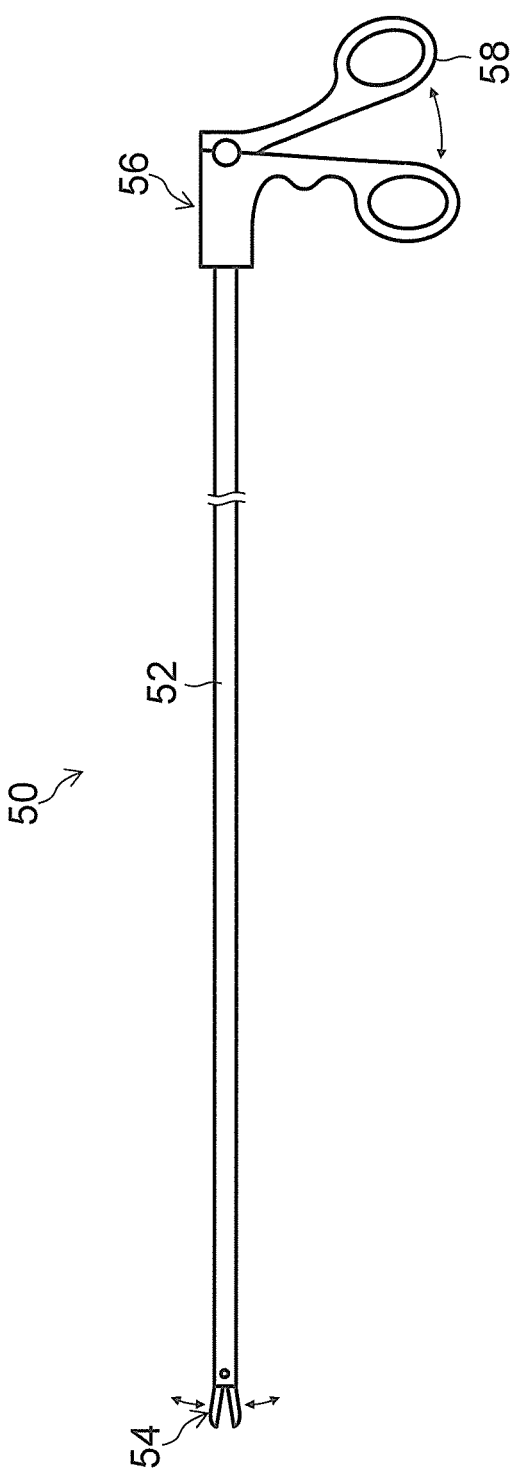
FIG. 4 is a schematic configuration diagram showing an example of a treatment tool.

FIG. 4 is a schematic configuration diagram showing an example of the treatment tool 50.

The treatment tool 50 includes: the linear insertion part 52 to be inserted into a body cavity; a treatment part 54 provided at a distal end of the insertion part 52; and a handle part (operation part) 56 provided at a proximal end of the insertion part 52. The treatment part 54 shown in FIG. 5 has a scissors structure, so that the treatment part 54 is opened and closed by opening-closing operation of the handle part 56. A gripping part 58 of the handle part 56 constitutes at least a part of an operation part of the treatment tool 50.

Here, the treatment tool 50 is not limited to the above, and forceps, a laser probe, a suture instrument, an electric knife, a needle holder, an ultrasound aspirator and so on, can be used as the treatment tool.

[Outer Tube 100]

Figure 5:
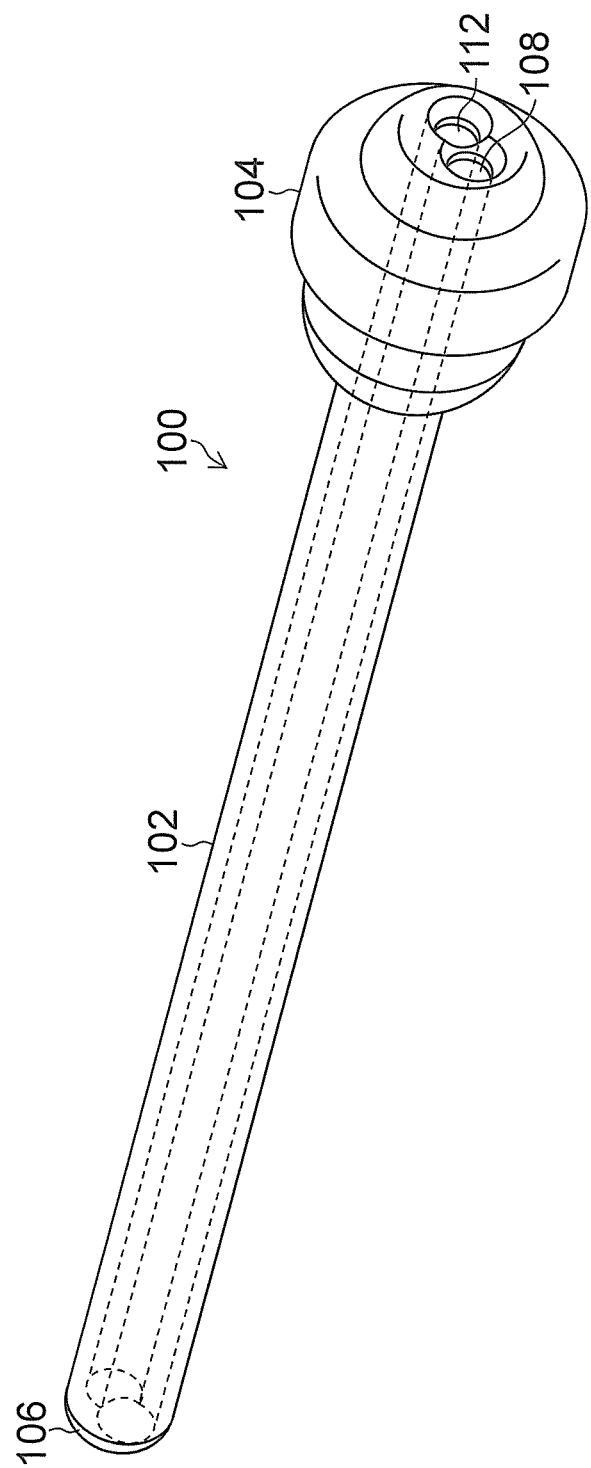
FIG. 5 is a perspective view showing an example of an outer tube.

FIG. 5 is a perspective view showing an example of the outer tube 100.

The outer tube 100 is penetrated through a body cavity wall of a patient to guide the insertion part 12 of the endoscope 10 and the insertion part 52 of the treatment tool 50 into a body cavity of the patient.

Figure 6:
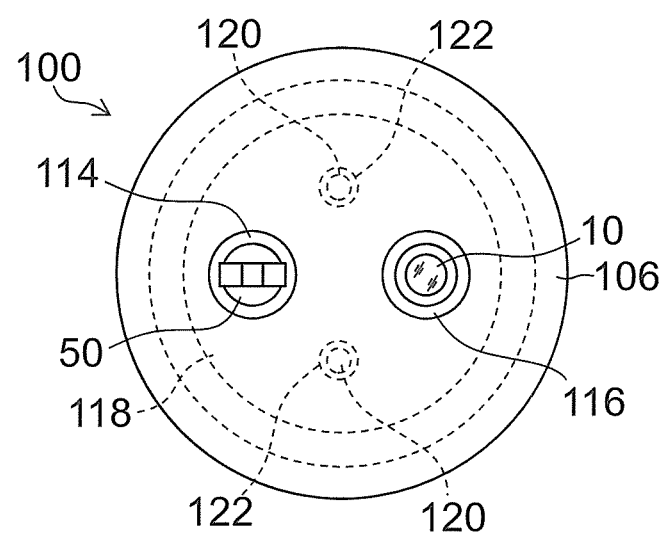
FIG. 6 is a front view of a distal end face of the outer tube into which the endoscope and the treatment tool are inserted.
Figure 7:
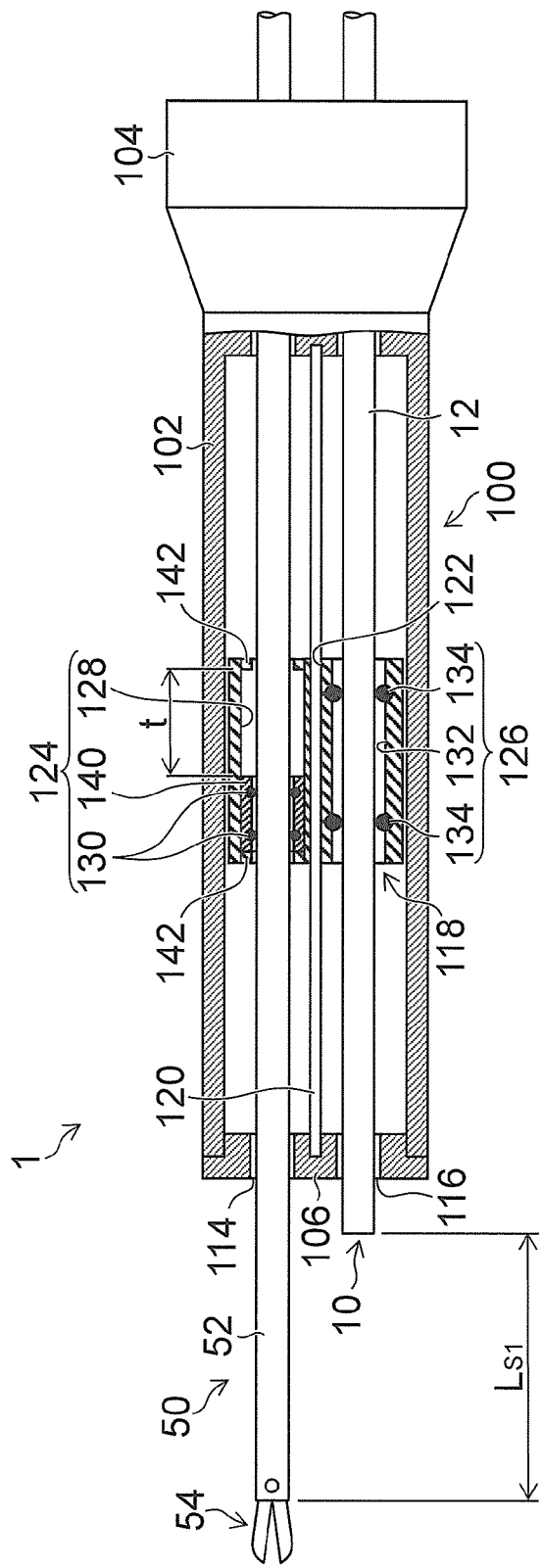
FIG. 7 is a side partial sectional view of the outer tube into which the endoscope and the treatment tool are inserted.
Figure 8:
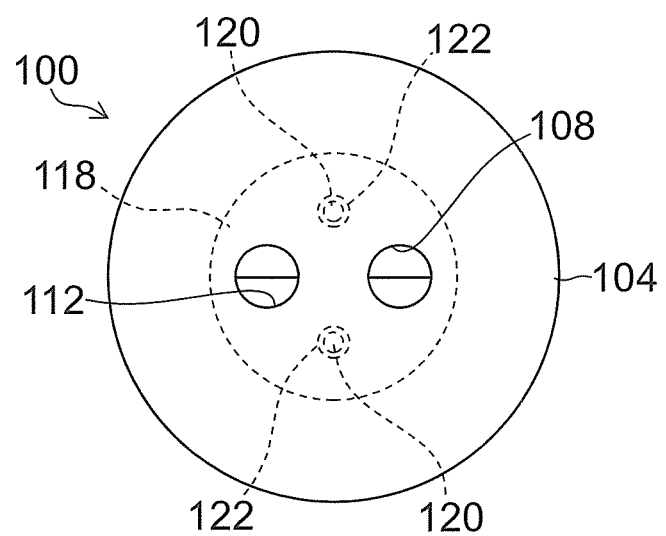
FIG. 8 is a front view of a proximal end face of the outer tube.

FIG. 6 is a front view of a distal end face of the outer tube 100 into which the endoscope 10 and the treatment tool 50 are inserted, FIG. 7 is a side partial sectional view of the outer tube 100 into which the endoscope 10 and the treatment tool 50 are inserted, and FIG. 8 is a front view of a proximal end face of the outer tube 100.

The outer tube 100 includes a cylindrical outer tube body 102. The outer tube body 102 is provided at its proximal end with a cap 104. The cap 104 houses a valve member that secures airtightness so that the valve member closes an opening at the proximal end of the outer tube body 102. The outer tube body 102 is provided at its distal end with a cap 106, and the cap 106 closes an opening at the distal end of the outer tube body 102.

As shown in FIGS. 5 and 8, the cap 104 is provided with a treatment tool entry port 108 through which the insertion part 52 of the treatment tool 50 is inserted into the outer tube body 102. The treatment tool entry port 108 has an inner diameter corresponding to an outer diameter of the insertion part 52 of the treatment tool 50 to be used.

In addition, the cap 104 is provided with an endoscope entry port 112 through which the insertion part 12 of the endoscope 10 is inserted into the outer tube body 102. The endoscope entry port 112 has an inner diameter corresponding to an outer diameter of the insertion part 12 of the endoscope 10 to be used.

As shown in FIG. 6, the cap 106 is provided with a treatment tool exit port 114 through which the insertion part 52 of the treatment tool 50 inserted into the outer tube body 102 is drawn out. The treatment tool exit port 114 has an inner diameter corresponding to the outer diameter of the insertion part 52 of the treatment tool 50 to be used. The treatment tool entry port 108 of FIG. 8 and the treatment tool exit port 114 of FIG. 6 are coaxially arranged so as to be parallel to an axis of the outer tube body 102. Accordingly, as shown in FIG. 7, the treatment tool 50 inserted from the treatment tool entry port 108 (refer to FIG. 8) is drawn out through the treatment tool exit port 114 (refer to FIG. 6). At this time, the insertion part 52 of the treatment tool 50 is drawn out parallel to the axis of the outer tube body 102.

In addition, the cap 106 of FIG. 6 is provided with an endoscope exit port 116 through which the insertion part 12 of the endoscope 10 inserted into the outer tube body 102 through the endoscope entry port 112 of FIG. 8 is drawn out. The endoscope exit port 116 has an inner diameter corresponding to the outer diameter of the insertion part 12 of the endoscope 10 to be used. The endoscope entry port 112 (refer to FIG. 8) and the endoscope exit port 116 (refer to FIG. 6) are coaxially arranged so as to be parallel to the axis of the outer tube body 102. Accordingly, as shown in FIG. 7, the endoscope 10 inserted from the endoscope entry port 112 (refer to FIG. 8) is drawn out through the endoscope exit port 116 (refer to FIG. 6). At this time, the insertion part 12 of the endoscope 10 is drawn out parallel to the axis of the outer tube body 102.

[Internal Structure of Outer Tube 100]

As shown in FIG. 7, the outer tube body 102 is provided inside with a slider (first movable object) 118 that is movable in a direction parallel to the axis of the outer tube body 102.

The slider 118 is formed into a columnar shape that can be housed in the outer tube body 102. The slider 118 is configured to be guided by a pair of guide shafts 120 and be movable in the outer tube body 102 in a direction parallel to the axis of the outer tube body 102.

Each of the guide shafts 120 is formed in a round-rod shape, and is arranged inside the outer tube body 102 (refer to FIG. 6). Moreover, proximal ends of the guide shafts 120 are supported by the cap 104, and distal ends of the guide shafts 120 are supported by the cap 106. The guide shafts 120 are arranged parallel to the axis of the outer tube body 102.

The slider 118 is provided with a pair of guide holes 122 through which the pair of guide shafts 120 can be inserted. The pair of guide holes 122 is arranged at the same interval as the arrangement interval of the pair of guide shafts 120 so as to be parallel to the axis of the outer tube body 102. The guide shafts 120 are inserted through the guide holes 122 to guide the slider 118.

The slider 118 includes a treatment tool holding part 124 that holds the insertion part 52 of the treatment tool 50 inserted into the outer tube body 102, and an endoscope holding part 126 that holds the insertion part 12 of the endoscope 10 inserted into the outer tube body 102.

The endoscope holding part 126 includes an endoscope holding hole 132 through which the insertion part 12 of the endoscope 10 is inserted, and a pair of O-rings 134 arranged in the endoscope holding hole 132.

The endoscope holding hole 132 is formed by penetrating the slider 118. The endoscope holding hole 132 is formed in parallel to the axis of the outer tube body 102, and is arranged coaxially with the endoscope entry port 112 and the endoscope exit port 116.

The pair of O-rings 134 is attached to two places, front and rear, inside the endoscope holding hole 132. Each of the O-rings 134 has an inner diameter slightly smaller than the outer diameter of the insertion part 12 of the endoscope 10.

The insertion part 12 of the endoscope 10 inserted into the outer tube body 102 from the endoscope entry port 112 is drawn out from the endoscope exit port 116 through the endoscope holding hole 132. The endoscope 10 passes through the O-rings 134 when passing through the endoscope holding hole 132. As described above, each of the O-rings 134 has the inner diameter slightly smaller than the outer diameter of the insertion part 12 of the endoscope 10. Thus, the insertion part 12 of the endoscope 10 is held in the endoscope holding hole 132 by elastic force of the O-rings 134 after passing through the endoscope holding hole 132.

Here, since holding here is achieved by elastic force of each of the O-rings 134, it is possible to arbitrarily adjust the holding position of the endoscope 10 with respect to the slider 118.

In addition, although the endoscope 10 is held by the elastic force of the O-rings 134, the frictional force between the O-rings 134 and the insertion part 12 of the endoscope 10 is set larger than the frictional force (corresponding to frictional force F1 between the outer tube body 102 and the slider 118) between the guide shafts 120 and the guide holes 122. Accordingly, the slider 118 and the insertion part 12 of the endoscope 10 integrally move with respect to the outer tube body 102.

The treatment tool holding part 124 includes: a treatment tool holding hole 128 through which the insertion part 52 of the treatment tool 50 is inserted; a sleeve (second movable object) 140 that is arranged in the treatment tool holding hole 128 and movable along the treatment tool holding hole 128 in an axial direction; and a pair of O-rings 130 that is arranged in the sleeve 140. The slider 118 and the sleeve 140 constitute a coupling member.

The treatment tool holding hole 128 is formed by penetrating the slider 118. The treatment tool holding hole 128 is formed in parallel to the axis of the outer tube body 102, and is arranged coaxially with the treatment tool entry port 108 and the treatment tool exit port 114.

The treatment tool holding hole 128 is provided at its both ends with an annular stopper ring 142. The stopper rings 142 and 142 prevent the sleeve 140 housed in the treatment tool holding hole 128 from coming out of the treatment tool holding hole 128. In addition, in the sleeve 140, an allowance amount t in the axial direction is set by the stopper rings 142 and 142. That is, the sleeve 140 is provided so as to be movable relative to the slider 118 by the allowance amount t between the respective stopper rings 142 and 142 provided at both ends of the treatment tool holding hole 128.

The sleeve 140 is formed in a cylindrical shape, and is housed inside the treatment tool holding hole 128 and is arranged coaxially with the treatment tool holding hole 128. That is, the sleeve 140 is arranged coaxially with the treatment tool entry port 108 and the treatment tool exit port 114. Accordingly, when the treatment tool 50 is inserted from the treatment tool entry port 108 along the axial direction, the insertion part 52 of the treatment tool 50 is inserted into an inner peripheral part of the sleeve 140.

The pair of O-rings 130 is attached to two places, front and rear, inside the sleeve 140. Each of the O-rings 130 has an inner diameter slightly smaller than the outer diameter of the insertion part 52 of the treatment tool 50.

The insertion part 52 of the treatment tool 50 inserted from the treatment tool entry port 108 into the outer tube body 102 is drawn out from the treatment tool exit port 114 through the treatment tool holding hole 128. The insertion part 52 passes through the O-rings 130 arranged in the inner peripheral portion of the sleeve 140 when passing through the treatment tool holding hole 128. Each of the O-rings 130 has the inner diameter slightly smaller than the outer diameter of the insertion part 52 of the treatment tool 50. Thus, the insertion part 52 is held by the sleeve 140 by elastic force of the O-rings 130 after passing through the O-rings 130.

Here, since holding here is achieved by elastic force of each of the O-rings 130, it is possible to arbitrarily adjust a holding position of the insertion part 52 of the treatment tool 50 with respect to the sleeve 140. That is, it is possible to arbitrarily adjust the holding position of the insertion part 52 of the treatment tool 50 with respect to the slider 118. FIG. 7 shows Ls1 that is a minimum projection length of the distal end of the insertion part 52 of the treatment tool 50 with respect to a distal end of the insertion part 12 of the endoscope 10.

In the treatment tool holding part 124, the sleeve 140 is integrated with the insertion part 52 of the treatment tool 50, so that the sleeve 140 moves in interlock with movement of the insertion part 52 of the treatment tool 50.

Here, if a frictional force (F3) between the sleeve 140 and the treatment tool holding hole 128 is greater than a frictional force (F2) between the insertion part 52 of the treatment tool 50 and the O-rings 130, the insertion part 52 slides between the O-rings 130 so that the sleeve 140 cannot move with respect to the slider 118. For this reason, the frictional force (F3) between the sleeve 140 and the treatment tool holding hole 128 is set less than the frictional force (F2) between the treatment tool 50 and the O-rings 130.

On the other hand, if the frictional force (F3) between the sleeve 140 and the treatment tool holding hole 128 is greater than the frictional force between the guide shaft 120 and the guide hole 122 (corresponding to the frictional force F1 between the outer tube body 102 and the slider 118), the slider 118 instead of the sleeve 140 moves with respect to the outer tube body 102 when the treatment tool 50 is moved. For this reason, the frictional force (F1) between the guide shaft 120 and the guide hole 122 is set greater than the frictional force (F3) between the sleeve 140 and the treatment tool holding hole 128.

In addition, the frictional force (F2) between the treatment tool 50 and the O-rings 130 is set greater than the frictional force (F1) between the guide shaft 120 and the guide hole 122.

That is, the frictional force (F1) between the guide shaft 120 and the guide hole 122, the frictional force (F2) between the treatment tool 50 and the O-rings 130, and the frictional force (F3) between the sleeve 140 and the treatment tool holding hole 128, are set to satisfy the following relationship of F2>F1>F3.

Accordingly, if movement of the insertion part 52 of the treatment tool 50 in the axial direction is equal to or less than the allowance amount t set by the pair of stopper rings 142 and 142, the slider 118 does not move so that the endoscope 10 also does not move together.

By providing the allowance amount t, it is possible to prevent an image in a screen from shaking when the insertion part 52 is slightly displaced in the axial direction (when back-and-forth movement at a small amplitude is performed), for example. As a result, it is possible to provide an easily visible image without shake.

<<Operation of Endoscopic Surgery Device 1>>

Figure 9:
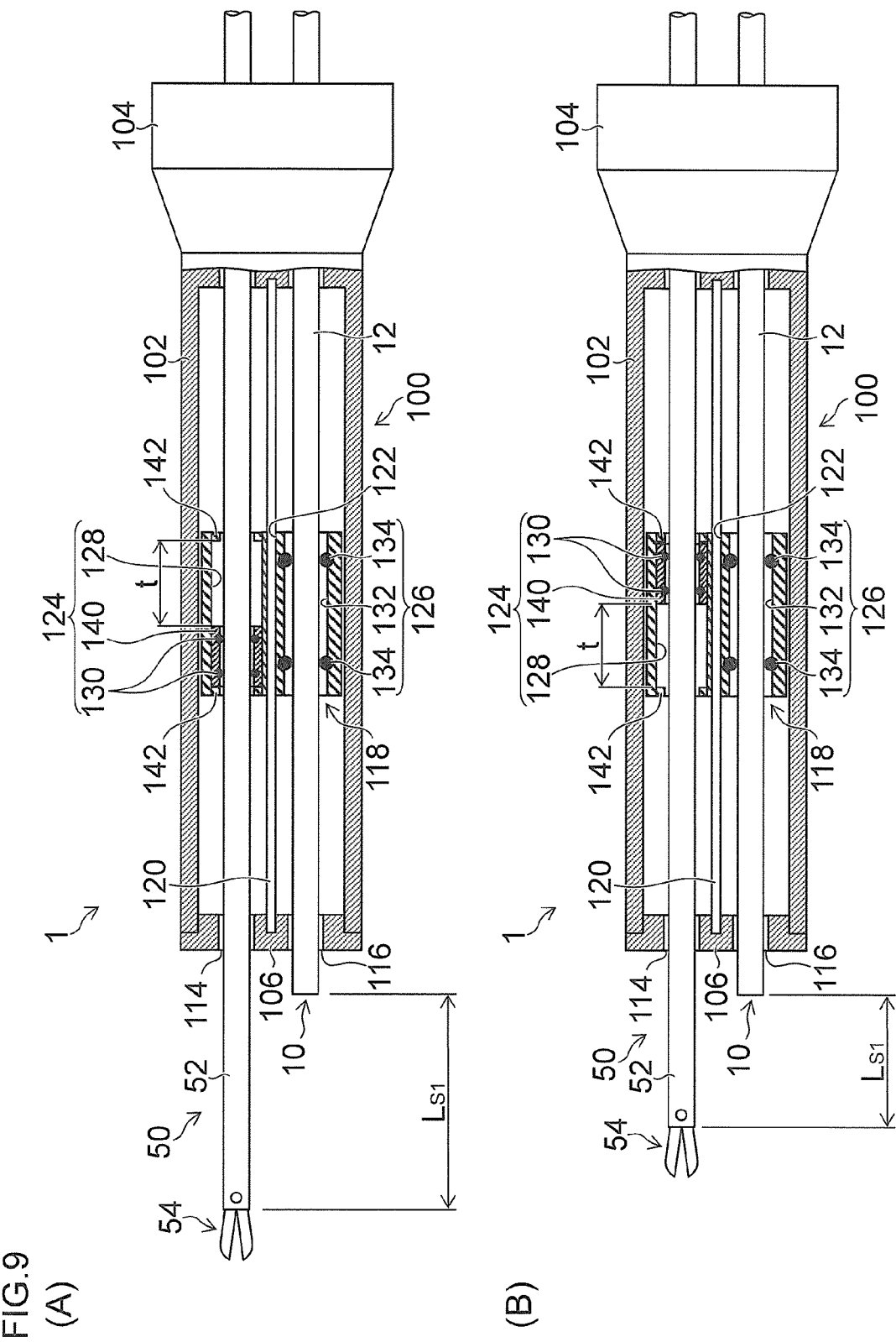
FIG. 9 is an illustration of describing a form of the endoscopic surgery device during use, in which an insertion part of the treatment tool is moved in an axial direction of the outer tube from a state illustrated in portion (A) to a state illustrated in portion (B).

FIG. 9 is an illustration of describing a mode when the endoscopic surgery device 1 is used. In FIG. 9, the insertion part 52 of the treatment tool 50 is moved in an axial direction of the outer tube 100 from a state illustrated in portion (A) to a state illustrated in portion (B).

The insertion part 12 of the endoscope 10 inserted into the outer tube 100 and the insertion part 52 of the treatment tool 50 are held in parallel to each other as well as held in parallel to the axis of the outer tube 100.

Here, the insertion part 52 of the treatment tool 50 is held by the sleeve 140, and the sleeve 140 is provided so as to be movable in the axial direction with respect to the slider 118. In addition, the frictional force (F3) between the sleeve 140 and the treatment tool holding hole 128, and the frictional force (F1) between the guide shaft 120 and the guide hole 122, are set so as to satisfy the relationship of F3<F1.

As a result, if movement of the insertion part 52 of the treatment tool 50 in the back-and-forth direction (axial direction) is within a range of the allowance amount t of the sleeve 140 defined by the pair of stopper rings 142 and 142, the endoscope 10 does not move in the back-and-forth direction and only the treatment tool 50 moves in the back-and-forth direction.

On the other hand, when the insertion part 52 of the treatment tool 50 is moved in the back-and-forth direction beyond the range of the allowance amount t, the slider 118 is pushed by the sleeve 140 to move integrally with the treatment tool 50. As a result, the insertion part 12 of the endoscope 10 moves in interlock with the treatment tool 50 in the back-and-forth direction.

Specifically, when the insertion part 52 of the treatment tool 50 moves in an advancing direction (distal end direction) beyond the allowance amount t of the sleeve 140, a distal end of the sleeve 140 abuts on the stopper ring 142 provided at a distal end of the treatment tool holding hole 128 and the slider 118 and the treatment tool 50 move integrally with each other in the distal end direction. As a result, the insertion part 12 of the endoscope 10 moves together with the treatment tool 50 in the distal end direction.

On the other hand, when the insertion part 52 of the treatment tool 50 moves in a retracting direction (proximal end direction) beyond the allowance amount t of the sleeve 140, a proximal end of the sleeve 140 abuts on the stopper ring 142 provided at a proximal end of the treatment tool holding hole 128 and the slider 118 and the treatment tool 50 move integrally with each other in the proximal end direction. As a result, the insertion part 12 of the endoscope 10 moves together with the treatment tool 50 in the proximal end direction.

Thus, according to the endoscopic surgery device 1, only when the treatment tool 50 is moved beyond the range of the allowance amount t, the endoscope 10 moves in the same direction in interlock with the treatment tool 50. Accordingly, movement of the treatment tool 50 at a small amplitude, such as slight shaking within the range of the allowance amount t, is not transmitted to the endoscope 10, whereby it is possible to provide a favorable endoscopic image without shake.

Here, as shown in portions (A) and (B) of FIG. 9, Ls1 varies in accordance with the allowance amount t. That is, Ls1 shown in the portion (A) of FIG. 9 is a maximum length of Ls1, and Ls1 shown in the portion (B) of FIG. 9 is a minimum length of Ls1.

<<Example of Use of Endoscopic Surgery Device 1>>

Figure 10:
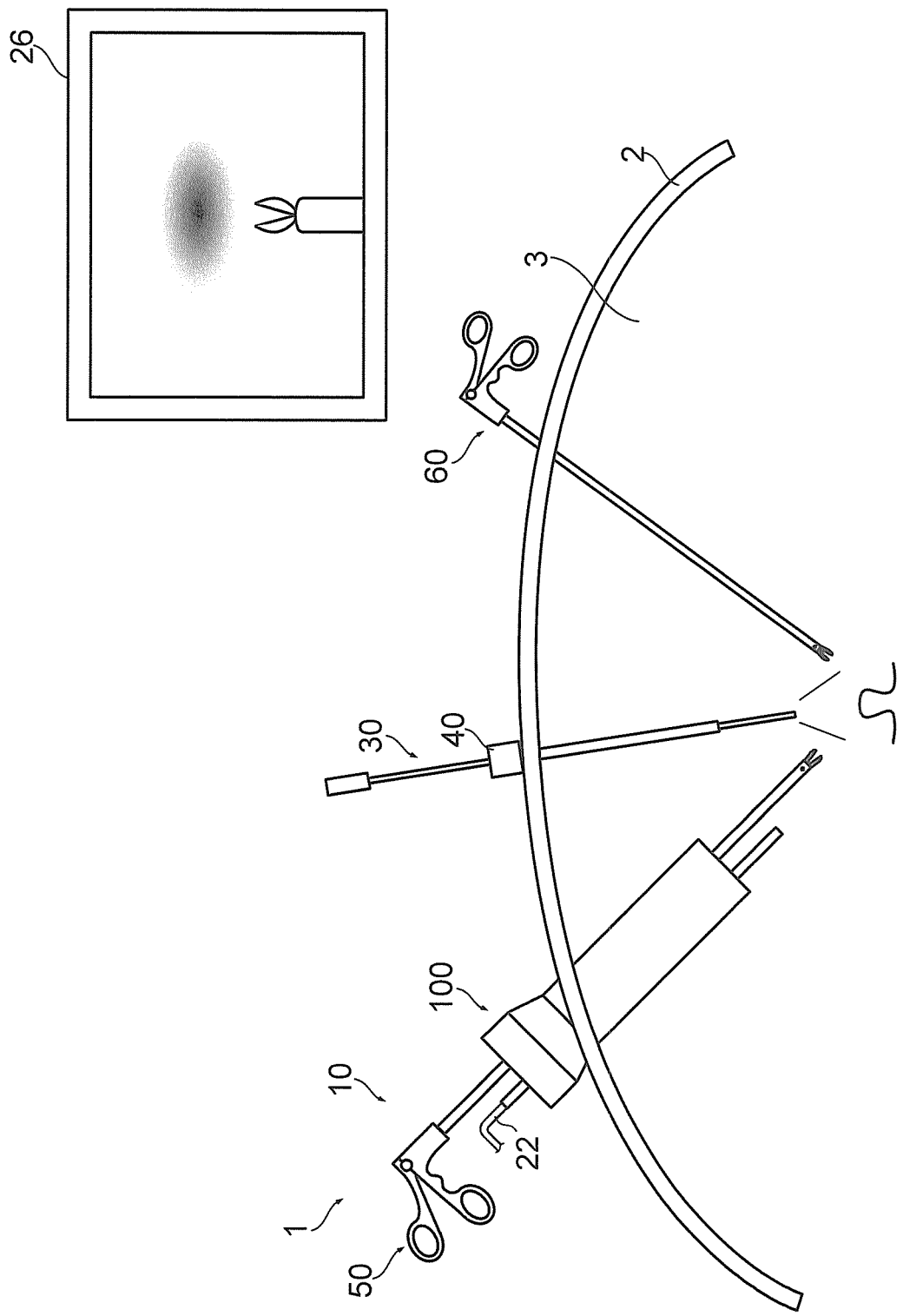
FIG. 10 is a schematic explanatory view showing an example of surgical procedure using the endoscopic surgery device.

FIG. 10 is a schematic view showing an example of surgical procedure using the endoscopic surgery device 1.

The present example shows a case where one surgeon performs treatment.

The endoscope 10 and the treatment tool 50 are inserted into a body cavity 3 through the outer tube 100 penetrating through a body cavity wall 2 of a patient. The endoscope 10 moves in interlock with movement of the treatment tool 50. Accordingly, an image of a site to be treated is always displayed in the display 26 and a field of view of the endoscope 10 can be moved by moving the treatment tool 50.

Since the endoscope 10 includes no illumination means, the needle light 30 is separately inserted into the body cavity 3 through the trocar 40 for a needle light as the illumination means. The body cavity 3 is irradiated with illumination light emitted from a distal end of the needle light 30. In the present example, one needle light 30 is shown, however, a plurality of needle lights 30 may be used if necessary. As described above, since the endoscope 10 is also operated by operation of the treatment tool 50, a scopist becomes unnecessary.

<<Feature of Endoscopic Surgery Device 1 of Embodiment>> a) First Feature

The insertion part 12 of the endoscope 10 and the insertion part 52 of the treatment tool 50 are coupled with each other by means of the coupling member composed of the slider 118 and the sleeve 140 which are arranged inside the outer tube body 102.

Accordingly, since the endoscope 10 moves in a back-and-forth direction in interlock with operation of the treatment tool 50 in the back-and-forth direction, it is possible to move the insertion part 12 of the endoscope 10 and the insertion part 52 of the treatment tool 50, which are inserted into the outer tube 100, back and forth in interlock with each other.

In addition, the insertion part 52 of the treatment tool 50 is coupled to the coupling member so as to move in an axial direction of the outer tube 100 with the allowance amount t with respect to the insertion part 12 of the endoscope 10.

Accordingly, if the insertion part 52 of the treatment tool 50 is moved in the back-and-forth direction within a range of the allowance amount t, the endoscope 10 does not move in the back-and-forth direction. By providing the allowance amount t, slight movement of the treatment tool 50 is not transmitted to the endoscope 10, whereby it is possible to acquire a favorable endoscopic image without shake.

b) Second Feature

In order to observe the treatment part 54 of the treatment tool 50 with the objective lens 16 and the imaging element 20 of the endoscope 10, as shown in FIG. 1, a projection length a of the distal end of the insertion part 52 of the treatment tool 50, projecting from the distal end of the outer tube 100, is set equal to or longer than a projection length b of the distal end of the insertion part 12 of the endoscope 10, projecting from the distal end of the outer tube 100.

In order to reduce the diameter of the outer tube 100, a distance c between centers of the insertion part 12 of the endoscope 10 and the insertion part 52 of the treatment tool 50 in the outer tube 100 is set shorter than a distance d between an axial center of the insertion part 52 of the treatment tool 50 and the gripping part 58 of the handle part 56 of the treatment tool 50. Accordingly, in the endoscopic surgery device 1, the gripping part 58 exists on an extension line in an axial direction of the insertion part 12 of the endoscope 10. That is, when the treatment tool 50 is operated in an insertion direction, the gripping part 58 may interfere with the proximal end of the insertion part 12.

In order to avoid that problem, this endoscopic surgery device 1 is configured so as to satisfy the following expressions: $Lt \leq Ls < Lh$, and $Lh \geq Ls1 + Ls + t$, where Lt is a length of the outer tube, Ls is a length of the hard part of the insertion part of the endoscope, Lh is a length of the hard part of the insertion part of the treatment tool, Ls1 is the minimum projection length of the distal end of the insertion part of the treatment tool with respect to the distal end of the insertion part of the endoscope, and t is the allowance amount.

That is, since the length Lh of the hard part of the insertion part of the treatment tool is equal to or longer than a length obtained by totaling the projection length Ls1, the length Ls of the insertion part 12 of the endoscope 10, and the allowance amount t, it is possible to reliably prevent the gripping part 58 of the handle part 56 of the treatment tool 50 from interfering with the cable 22 at the proximal end of the insertion part 12 of the endoscope 10 at the time of operation of inserting the treatment tool 50 into the outer tube 100. In addition, if the treatment tool 50 is moved in a back-and-forth direction beyond a range of the allowance amount t, since the endoscope 10 also moves in the same direction in interlock with the treatment tool 50, the handle part 56 of the treatment tool 50 does not interfere with the proximal end of the endoscope.

Figure 11:
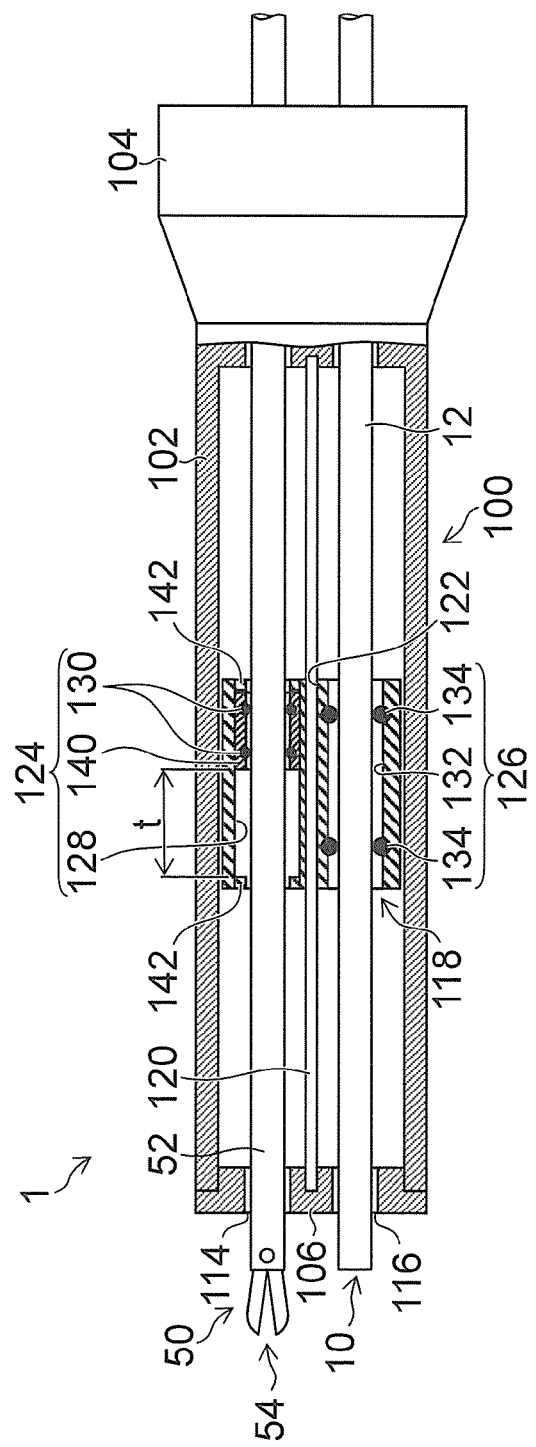
FIG. 11 is a partial sectional view showing a form of the endoscopic surgery device in a case where minimum projection length Ls1 is zero.

FIG. 11 shows a mode of the endoscopic surgery device 1 in a case where the minimum projection length Ls1 is zero.

Even if the minimum projection length Ls1 is set at zero, there may be a case where the treatment part 54 of the treatment tool 50 can be observed with the objective lens 16 and the imaging element 20 of the endoscope 10.

It is preferable that the minimum projection length Ls1 be a length which allow at least the distal end of the insertion part 52 of the treatment tool 50 to be positioned in a field of view of the objective lens 16 of the endoscope 10. Accordingly, it is possible to obtain an endoscopic image of the treatment part 54 including the distal end of the insertion part 52 of the treatment tool 50.

In addition, it is preferable that the minimum projection length Ls1 be set at 50 mm, and the allowance amount t is set at 20 mm. Since this range is a substantial range of use where a surgeon usually operates, the surgeon can operate the treatment tool without discomfort.

[Example of Length of Endoscopic Surgery Device 1]

The endoscopic surgery device 1 can satisfy the following expressions: $Lt \leq Ls < Lh$, and $Lh \geq Ls1 + Ls + t$, under conditions where:

Length Lt of the outer tube 100 is 160 mm;

length Ls of the hard part of the insertion part 12 of the endoscope 10 is 250 mm;

length Lh of the hard part of the insertion part 52 of the treatment tool 50 is 360 mm;

the minimum projection length Ls1 is 50 mm; and the allowance amount t is 20 mm.

<<Method of inserting Endoscope 10 and Treatment Tool 50 into Outer Tube 100>>

Figure 12:
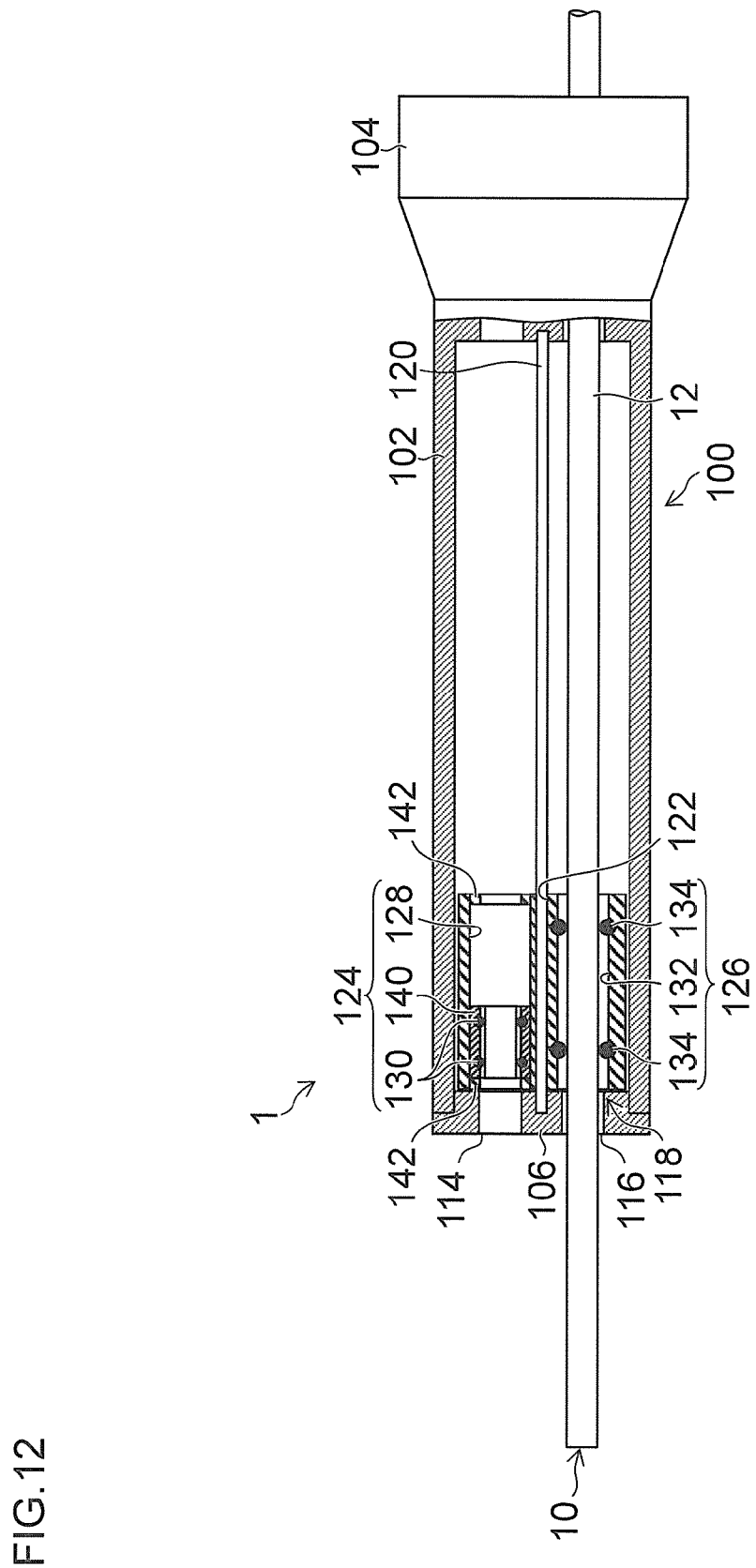
FIG. 12 is a partial sectional view of the outer tube into which an insertion part of the endoscope is inserted.
Figure 13:
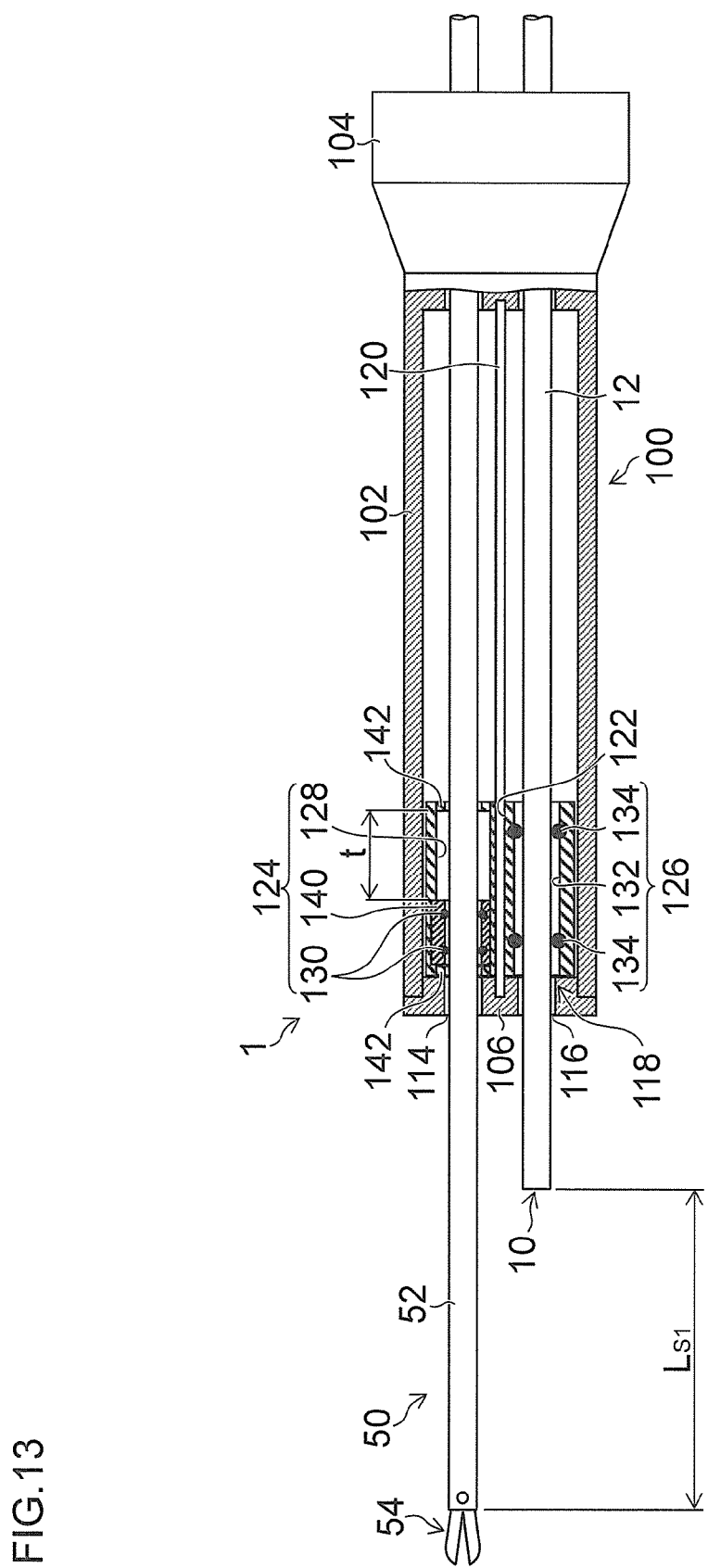
FIG. 13 is a partial sectional view of the outer tube into which an insertion part of the treatment tool is inserted.

FIG. 12 is a partial sectional view of the outer tube 100 into which the insertion part 12 of the endoscope 10 is inserted, and FIG. 13 is a partial sectional view of the outer tube 100 into which the insertion part 12 of the endoscope 10 and the insertion part 52 of the treatment tool 50 are inserted.

First, as shown in FIG. 12, the insertion part 12 of the endoscope 10 is inserted from the endoscope entry port 112 (refer to FIG. 8) (first insertion step). The insertion part 12 inserted from the endoscope entry port 112 passes through the outer tube body 102 and is drawn out from the endoscope exit port 116. At that time, the insertion part 12 passes through the endoscope holding hole 132 formed in the slider 118 which is arranged in the outer tube body, and is drawn out from the endoscope exit port 116. The endoscope holding hole 132 is provided with the O-rings 134, and the insertion part 12 inserted into the endoscope holding hole 132 is held by the slider 118 by elastic force of the O-rings 134.

Next, as shown in FIG. 13, the insertion part 52 of the treatment tool 50 is inserted from the treatment tool entry port 108 (second insertion step). The insertion part 52 inserted from the treatment tool entry port 108 passes through the outer tube body 102 and is drawn out from the treatment tool exit port 114. At that time, the insertion part 52 is held by the sleeve 140 by elastic force of the O-rings 130. In this case, the minimum projection length Ls1 may be set zero or more and 70 mm or less, for example. Then, the treatment tool 50 is moved in a removal direction to position the endoscope 10 and the treatment tool 50 at a use position of FIG. 7.

In an insertion method of the embodiment, the insertion part 12 of the endoscope 10, which is shorter in length than the insertion part of the treatment tool 50, is first inserted into the outer tube 100, and then the insertion part 52 of the treatment tool 50 is inserted, whereby the endoscope 10 does not interfere with the treatment tool 50. In addition, when the insertion part 52 of the treatment tool 50 is inserted, the insertion part 12 of the endoscope 10 does not obstruct the insertion part of the treatment tool. Thus, it is possible to smoothly insert the treatment tool 50 into the outer tube 100 without bending the insertion part 12 of the endoscope 10.

<<Method of Removing Endoscope and Treatment Tool from Outer Tube 100>>

First, the insertion part 52 of the treatment tool 50 is moved in the removal direction from a state of FIG. 7. Then, the sleeve 140 abuts on the stopper ring 142 on a proximal end side, and subsequently the slider 118 moves together with the insertion part 52 to a proximal end side of the outer tube 100. When the slider 118 abuts on the proximal end of the outer tube 100 to restrict the movement of the slider 118, the insertion part 52 starts being removed from the slider 118 to be ultimately removed from the outer tube 100 (first removal step).

Next, when the insertion part 12 of the endoscope 10 is moved in the removal direction, the insertion part 12 starts being removed from the slider 118 to be ultimately removed from the outer tube 100 (second removal step).

In a removal method of the embodiment, the insertion part 52 of the treatment tool 50, which is longer in length than the insertion part of the endoscope 10, is first removed from the outer tube 100, and then the insertion part 12 of the endoscope 10 is removed, whereby the endoscope 10 does not interfere with the treatment tool 50. In addition, when the insertion part 52 of the treatment tool 50 is removed, the insertion part 12 of the endoscope 10 does not obstruct the insertion part of the treatment tool. As a result, it is possible to smoothly remove the treatment tool 50 from the outer tube 100 without bending the insertion part 12 of the endoscope 10.

What is claimed is:

1. An endoscopic surgery device comprising:
an endoscope which includes a linear insertion part and includes an imaging sensor configured to observe a body cavity;
a treatment tool including a linear insertion part having a proximal end provided with an operation part; and
an outer tube which is configured to allow each of the insertion part of the endoscope and the insertion part of the treatment tool to be movable back and forth, wherein the insertion part of the endoscope and the insertion part of the treatment tool are coupled with each other by a coupling part that is arranged inside the outer tube, the insertion part of the endoscope and the insertion part of the treatment tool are in a coupled state so as to move in an axial direction of the outer tube with an allowance amount, when either one of the insertion part of the endoscope and the insertion part of the treatment tool move back and forth within the allowance amount, then another one of the insertion part of the endoscope and the insertion part of the treatment tool does not move back and forth, and when either one of the insertion part of the endoscope and the insertion part of the treatment tool move back and forth beyond the allowance amount, then another one of the insertion part of the endoscope and the insertion part of the treatment tool will move back and forth,
wherein the endoscopic surgery device satisfies expressions of Lt≤Ls<Lh, and Lh≥Ls1+Ls+t, where
Lt (mm) is a length of the outer tube, Ls (mm) is a length of a hard part of the insertion part of the endoscope, Lh (mm) is a length of a hard part of the insertion part of the treatment tool, Ls1 (mm) is a minimum projection length of a distal end of the insertion part of the treatment tool with respect to a distal end of the insertion part of the endoscope, and t (mm) is the allowance amount of the insertion part of the treatment tool with respect to the insertion part of the endoscope,
wherein the endoscopic surgery device further comprises:
a coupling member constituting the coupling part that is arranged inside the outer tube and is configured to couple the insertion part of the endoscope to the insertion part of the treatment tool to allow the insertion part of the treatment tool to move in an axial direction of the outer tube with the allowance amount with respect to the insertion part of the endoscope,
wherein the coupling member includes:
a first movable object which is configured to be movable in the axial direction of the outer tube and hold the insertion part of the endoscope inserted into the outer tube; and
a second movable object which is provided in the first movable object, configured to hold the insertion part of the treatment tool inserted into the outer tube, and move in the axial direction of the outer tube by the allowance amount with respect to the first movable object.

2. The endoscopic surgery device according to claim 1, wherein the minimum projection length Ls1 satisfies Ls1≥0.

3. The endoscopic surgery device according to claim 2, wherein the minimum projection length Ls1 is a length with which at least the distal end of the insertion part of the treatment tool is positioned in an observation field of view of the endoscope.

4. The endoscopic surgery device according to claim 1, wherein a distance between centers of the insertion part of the endoscope and the insertion part of the treatment tool in the outer tube is set shorter than a distance between an axial center of the insertion part of the treatment tool and at least a part of the operation part of the treatment tool.

5. The endoscopic surgery device according to claim 1, wherein the distal end of the insertion part of the treatment tool has a treatment part, and the operation part of the treatment tool is a handle part configured to operate the treatment part.

6. The endoscopic surgery device according to claim 1, wherein a flexible cable is coupled to a proximal end of the insertion part of the endoscope.

7. The endoscopic surgery device according to claim 1, wherein the distal end of the insertion part of the endoscope has the image sensor.

8. The endoscopic surgery device according to claim 1, wherein
the first movable object is engaged with the outer tube with a first frictional force, and
the second movable object is engaged with the insertion part of the treatment tool with a second frictional force greater than the first frictional force, engaged with the first movable object with a third frictional force less than the first frictional force, and slides against the first movable object by the allowance amount.

9. A method of inserting the endoscope and the treatment tool into the outer tube by using the endoscopic surgery device according to claim 1, the method comprising:
a first insertion step of inserting the insertion part of the endoscope into the outer tube; and
a second insertion step of inserting the insertion part of the treatment tool into the outer tube into which the insertion part of the endoscope has been inserted.

10. A method of removing the endoscope and the treatment tool from the outer tube by using the endoscopic surgery device according to claim 1, the method comprising:
a first removal step of removing the insertion part of the treatment tool from the outer tube; and
a second removal step of removing the insertion part of the endoscope from the outer tube from which the insertion part of the treatment tool has been removed.

* * * * *